United States Patent
Salo et al.

(10) Patent No.: US 7,953,485 B2
(45) Date of Patent: *May 31, 2011

(54) THERAPY CONTROL BASED ON THE RATE OF CHANGE OF INTRACARDIAC IMPEDANCE

(75) Inventors: Rodney W. Salo, Fridley, MN (US); Joseph M. Pastore, Woodbury, MN (US); Jeffrey E. Stahmann, Ramsey, MN (US); Jesse W. Hartley, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 632 days.

This patent is subject to a terminal disclaimer.

(21) Appl. No.: 12/105,219

(22) Filed: Apr. 17, 2008

(65) Prior Publication Data

US 2008/0249583 A1    Oct. 9, 2008

Related U.S. Application Data

(63) Continuation of application No. 11/169,339, filed on Jun. 29, 2005, now Pat. No. 7,376,463.

(51) Int. Cl.
*A61N 1/362* (2006.01)
(52) U.S. Cl. ........................................................ 607/17
(58) Field of Classification Search ................. 607/9, 17, 607/18, 116
See application file for complete search history.

(56) References Cited

U.S. PATENT DOCUMENTS

| 4,548,209 | A |  | 10/1985 | Wielders et al. |
|-----------|---|---|---------|-----------------|
| 4,733,667 | A | * | 3/1988  | Olive et al. ............ 607/24 |
| 5,782,884 | A |  | 7/1998  | Stotts et al. |
| 6,278,894 | B1 |  | 8/2001 | Salo et al. |
| 7,146,208 | B2 |  | 12/2006 | Holmstrom et al. |
| 7,171,258 | B2 |  | 1/2007 | Goode |
| 7,376,463 | B2 | * | 5/2008 | Salo et al. ............ 607/17 |
| 2007/0005114 | A1 |  | 1/2007 | Salo et al. |

OTHER PUBLICATIONS

"U.S. Appl. No. 11/169,339 Notice of Allowance mailed Jan. 15, 2008", 9 pgs.
"U.S. Appl. No. 11/169,339 Non-Final Office Action mailed Jun. 26, 2007", 12 pgs.
"U.S. Appl. No. 11/169,339 Response filed Oct. 4, 2007 to Non-Final Office Action Mailed Jun. 26, 2007", 17 Pages.

* cited by examiner

*Primary Examiner* — Carl H Layno
*Assistant Examiner* — Brian T Gedeon
(74) *Attorney, Agent, or Firm* — Schwegman, Lundberg & Woessner, P.A.

(57) ABSTRACT

A system comprising a medical device that includes an impedance measurement circuit adapted to be coupled to implantable electrodes to obtain an intracardiac impedance signal between electrodes, a therapy circuit operable to deliver a therapy to a subject, and a controller circuit coupled to the impedance measurement circuit and the therapy circuit. The controller circuit determines a time rate of change of the intracardiac impedance signal and adjusts at least one parameter related to therapy in a manner that alters the rate of change.

20 Claims, 7 Drawing Sheets

THERAPY CONTROL BASED ON THE RATE OF CHANGE OF INTRACARDIAC IMPEDANCE

This application is a Continuation of U.S. application Ser. No. 11/169,339, now U.S. Pat. No. 7,376,463, filed on Jun. 29, 2005, which is incorporated herein by reference.

TECHNICAL FIELD

The field generally relates to implantable medical devices and, in particular, but not by way of limitation, to systems and methods for detecting events related to cardiac activity through monitoring intracardiac impedance.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), and devices that include a combination of pacing and defibrillation including cardiac resynchronization therapy. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events include heart chamber expansions or contractions. By monitoring cardiac signals indicative of expansions or contractions, IMDs are able to detect abnormally slow heart rate, or bradycardia. The IMDs are also able to detect abnormally rapid heart rate, or tachyarrhythmia. The IMDs are further able to detect differences in time between contractions of the left and right ventricles and to provide pacing therapy to resynchronize contractions of the left and right ventricles. However, proper resynchronization does not necessarily involve merely pacing the left and right ventricles simultaneously. Instead, there is a need to pace in a manner that improves the efficacy of the contractions. The present inventors have recognized a need for improved sensing of events related to cardiac activity.

SUMMARY

This document discusses, among other things, systems and methods for detecting events related to cardiac activity. A system embodiment includes a medical device. The medical device includes an impedance measurement circuit adapted to be coupled to implantable electrodes to obtain an intracardiac impedance signal between electrodes, a therapy circuit operable to deliver a therapy to a subject, and a controller circuit coupled to the impedance measurement circuit and the therapy circuit. The controller circuit determines a time rate of change of the intracardiac impedance signal and adjusts at least one parameter related to therapy in a manner that alters the rate of change.

A method embodiment includes sensing at least one intracardiac impedance signal of a patient using a medical device, measuring a rate of change of the intracardiac impedance signal with respect to time, and adjusting at least one therapy parameter provided to the patient in a manner that alters the rate of change.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
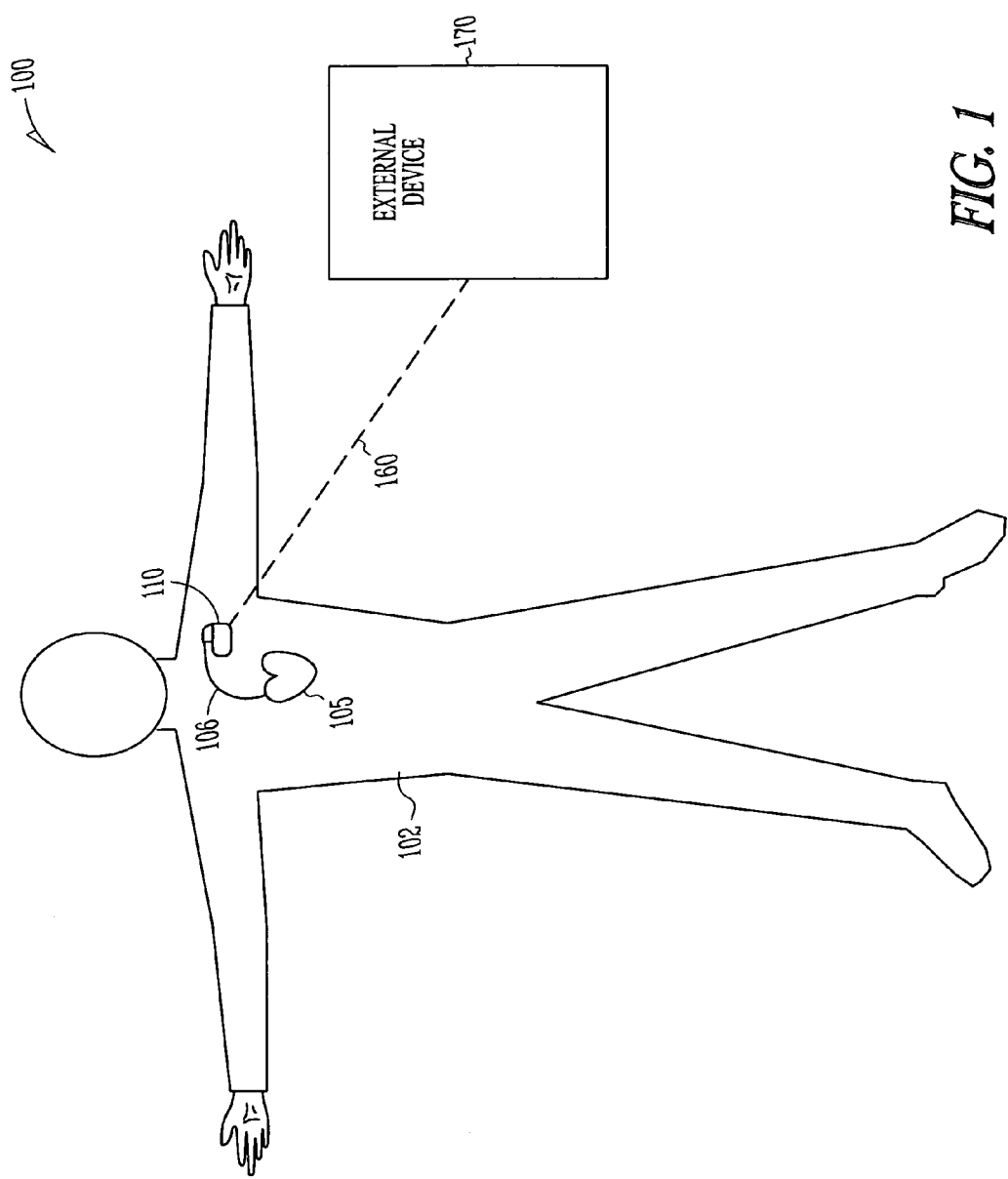
FIG. 1 illustrates an embodiment of portions of a system including an implantable medical device.

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

This document discusses systems and methods for controlling cardiac therapy using sensed intracardiac impedance. The various regions of an asynchronous left ventricle typically do not contract simultaneously. Instead, myocytes of the different regions typically shorten and lengthen asynchronously with respect to each other. This results in a prolonged contraction. The prolonged contraction requires more time to create a useful pressure to begin ejection of blood from heart chambers and more time from the beginning to the end of the contraction. As a result, the ejection force in an asynchronous left ventricle is lessened along with corresponding decreases in the peak value of a rate of volume change with respect to time (dV/dt) and the peak value of a rate of pressure change with respect to time (dP/dt). When the left ventricle is re-coordinated, the peak values are increased and maximum synchrony of contraction will result in a maximum left ventricle dV/dt or dP/dt. A measure of dV/dt in the left ventricle is directly related to the peak blood flow through the aorta and is thus a measure of left ventricle contraction strength. Rate of pressure change dP/dt is an after-load independent measure of left ventricular contraction strength or "contractility" independent of dV/dt. Both peak positive dV/dt and dP/dt are measures of contraction strength that occur at different times during the contraction. However, it is impractical to measure dP/dt in the left ventricle using a sensor such as a pressure transducer because placing the sensor in the left ventricle increases a potential for thrombosis and creates a possibility of a resulting stroke.

The present system and methods avoid this problem by deriving the efficacy of the heart contractions from the impedance measured within the heart, i.e., intracardiac impedance. The volume of blood, V, in a heart chamber such as the left ventricle is linearly related to the inverse of the measured impedance of the heart chamber by the formula:

$$V = \frac{\rho L^2}{Z},$$

where $\rho$ is blood resistivity and L is the distance between impedance measuring electrodes. Therefore, for a change of intracardiac impedance that is much less than the value of the intracardiac impedance itself (i.e., $dZ \ll Z$), a measured rate of change of blood volume can be determined from a measured negative rate of change of intracardiac impedance ($dV=-dZ$).

The intracardiac impedance is measured using a medical device. The impedance is measured between implantable electrodes placed in or near the heart chamber of interest. Alternatively, the impedance is measured between implantable electrodes placed within the thorax such that a component of the resulting impedance represents cardiac impedance. Information about the rate of change of blood volume can be determined either by converting the impedance to volume or by using the measured unprocessed, or "raw," impedance signal.

FIG. 1 illustrates an embodiment of portions of a system 100 that uses an implantable medical device (IMD) 110. As one example, the system 100 shown is used to treat a cardiac arrhythmia. The IMD 110 includes an electronics unit coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. Other examples include drug therapy device such as drug pumps, neural stimulation devices, and ventricular assist devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to MD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing electrical activity of the heart 105.

Figure 2:
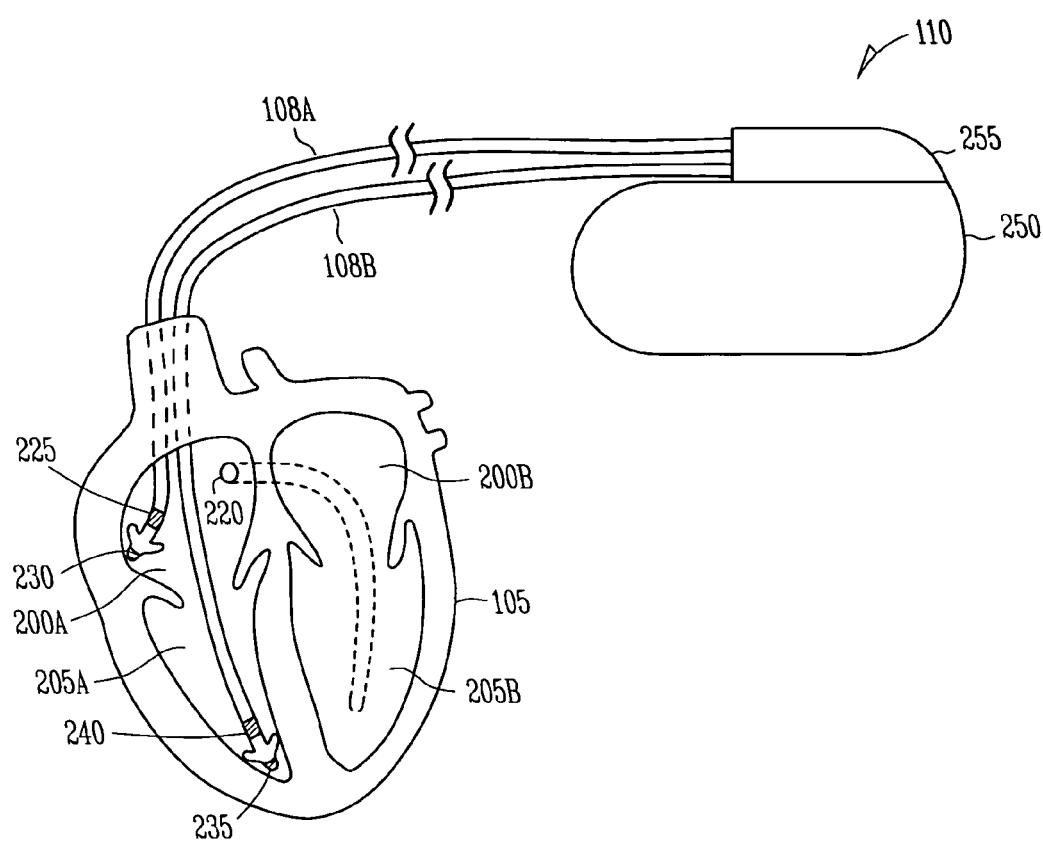
FIG. 2 illustrates an implantable medical device coupled by one or more leads to a heart.

FIG. 2 illustrates an IMD 110 coupled by one or more leads 108A-B to heart 105. Heart 105 includes a right atrium 200A, a left atrium 200B, a right ventricle 205A, a left ventricle 205B, and a coronary vein 220 extending from right atrium 200A. In this embodiment, atrial lead 108A includes electrodes (electrical contacts, such as ring electrode 225 and tip electrode 230) disposed in, around, or near an atrium 200A of heart 105 for sensing signals, or delivering pacing therapy, or both, to the atrium 200A. Lead 108A optionally also includes additional electrodes, such as for delivering atrial cardioversion, atrial defibrillation, ventricular cardioversion, ventricular defibrillation, or combinations thereof to heart 105. Lead 108A optionally further includes additional electrodes for delivering pacing or resynchronization therapy to the heart 105.

Ventricular lead 108B includes one or more electrodes, such as tip electrode 235 and ring electrode 240, for delivering sensing signals, for delivering pacing therapy, or for both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally further includes additional electrodes for delivering pacing or resynchronization therapy to the heart 105.

Other forms of electrodes include meshes and patches which may be applied to portions of heart 105 or which may be implanted in other areas of the body to help "steer" electrical currents produced by IMD 110. In one embodiment, one of atrial lead 108A or ventricular lead 108B is omitted, i.e., a "single chamber" device is provided, rather than the dual chamber device illustrated in FIG. 2. In another embodiment, additional leads are provided for coupling the IMD 110 to other heart chambers and/or other locations in the same heart chamber as one or more of leads 108A-B. The present methods and systems will work in a variety of configurations and with a variety of electrical contacts or "electrodes." Sensing among different sets of electrodes often provides directional information regarding the propagation of cardiac signals and is often referred to as sensing among different vectors. For example, sensing from an electrode placed proximal to the right atrium 200A to an electrode placed proximal to the right ventricle 205A would be one vector, sensing from the right atrium 200A to the left atrium 200B would be a second vector, and sensing from the right ventricle 205A to a can electrode 250, or a header electrode 255, would be a third vector.

The medical device measures intracardiac impedance between implantable electrodes placed in or near the heart chamber of interest. As an example, the intracardiac impedance of the left ventricle 205B is measured between an electrode placed in a coronary vein 220 and an electrode placed in a right ventricle 205A. In another example, the intracardiac impedance of the right ventricle 205A is measured between an electrode placed at the apex of the right ventricle 205A and an electrode placed in the right atrium 200A. Based on the measure of a rate of change of intracardiac impedance, the location of electrical cardiac rhythm management therapy, the timing of the therapy, or both the location and timing of the therapy can be modified periodically or continuously to increase or maximize dV/dt and therefore increase or maximize the strength of contraction of the heart.

Figure 3:
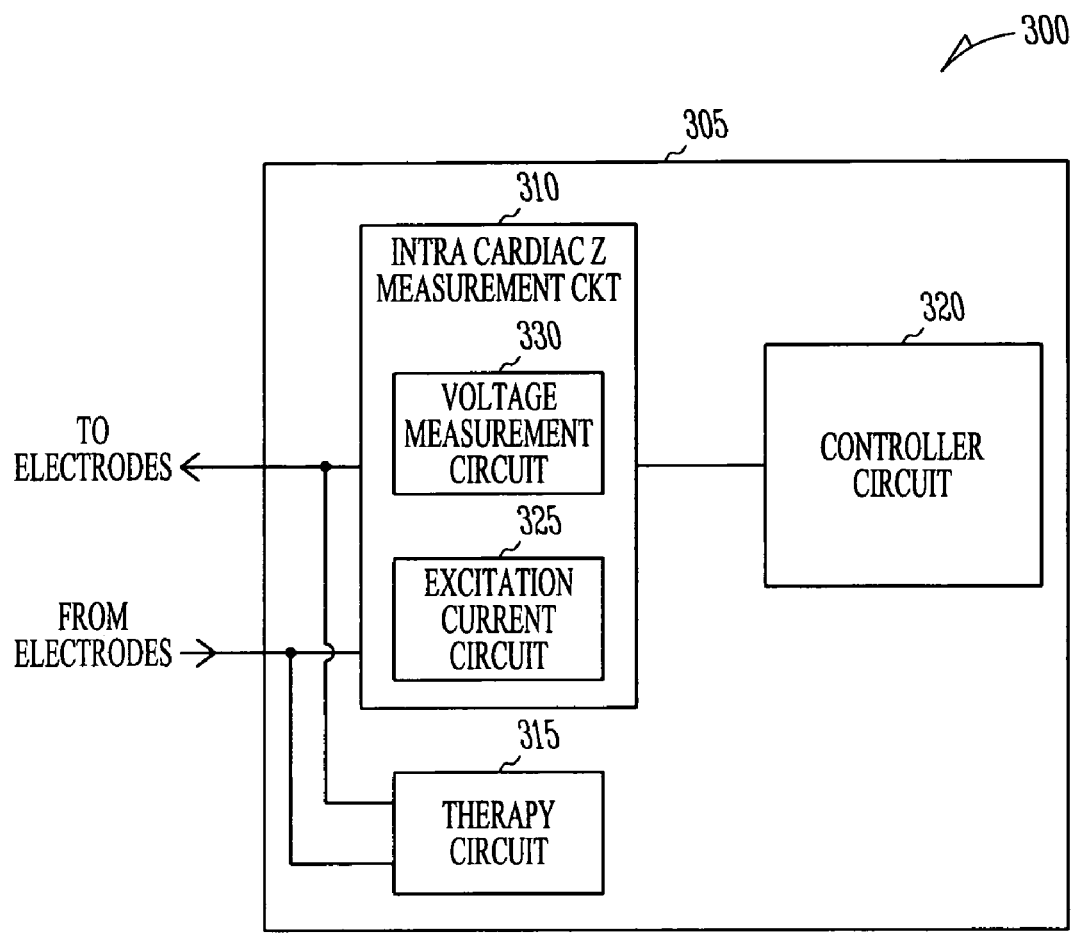
FIG. 3 shows a block diagram of an embodiment of a system to control cardiac therapy using sensed intracardiac impedance.

FIG. 3 shows a block diagram of an embodiment of a system 300 to control cardiac therapy using sensed intracardiac impedance. The system 300 includes a medical device 305. In some examples, the medical device 305 is implantable. The medical device 305 includes an intracardiac impedance measurement circuit 310, therapy circuit 315, and a controller circuit 320 coupled to the impedance measurement circuit 310 and therapy circuit 315. The impedance circuit 310 is coupled to implantable electrodes in order to obtain an intracardiac impedance signal between electrodes. In some examples, the intracardiac impedance measurement circuit 310 is coupled to a plurality of implantable electrodes and includes an excitation current circuit 325 and a voltage measurement circuit 330 coupled to the controller circuit 320. The excitation current circuit 325 delivers a specified excitation current using the implantable electrodes and the voltage measurement circuit 330 measures a voltage resulting from the excitation current. The resulting voltage may be measured using electrodes that are the same or different from the electrodes used to deliver the excitation current. For example, the excitation current could be delivered between ring electrodes on the leads on FIG. 2, and the voltage could be measured using either the same ring electrodes or measured between the tip electrodes. To avoid unintended stimulation of the heart, the magnitude of the current is small (e.g., 1-2 microamps) or the pulse width of the applied excitation current is small (e.g., 1 milliamp, 15 microsecond pulse width, 47 millisecond period). This excitation current can be kept small enough to satisfy typical leakage current requirements of an implantable device.

Similarly, a biphasic current waveform can be used to promote charge balance. It is important to maintain a DC current level as low as possible to limit corrosion in metal electrodes. The current leakage levels to limit corrosion are typically lower than the leakage limits for patient safety. Common practice to limit DC current is to capacitively couple the system/electrode interface. Using a biphasic waveform to promote charge balance further limits the corrosion. An additional reason that biphasic or symmetric waveforms are desirable is that they cause less interference with the internal sense-amps or with external sensing equipment, such as ECG machines. Descriptions of systems and methods using biphasic or symmetric waveforms to measure impedance are found in Hartley et al., U.S. Pat. No. 6,076,015, entitled, "Rate Adaptive Cardiac Rhythm Management Device Using Transthoracic Impedance," which is incorporated herein by reference.

The therapy circuit 315 delivers a therapy to a patient. In some examples, the therapy circuit 315 is coupled to the electrodes to provide pacing and/or defibrillation energy in conjunction with the electrodes disposed in or near a heart. The electrodes are used along with sense amplifiers for sensing electrical activity of a heart. In some examples, the medical device is a neural stimulation device and the therapy circuit 315 is coupled to the electrodes to provide energy for neural stimulation, such as a vagal nerve stimulation device. In some examples, the therapy circuit initiates delivery of a drug therapy, such as from a drug reservoir or from a drug patch of an iontophoretic device.

The controller circuit 320 is coupled to the impedance measurement circuit 310 and the therapy circuit 315. The controller circuit 320 determines a time rate of change of the intracardiac impedance signal, and adjusts at least one parameter related to therapy in a closed feedback loop manner that alters a peak value of the rate of change. In some examples, the parameters are adjusted in a manner that tends to increase or maximize the rate of change. In some examples, the parameters are adjusted in a manner that decreases the peak value of the rate of change of intracardiac impedance or to maintain a peak value of the rate of change between a predetermined range of values. In some examples, the controller circuit 320 computes an approximation of a time derivative of intracardiac impedance by measuring a change in intracardiac impedance per unit of time. In some examples, the system 300 includes a peak detector circuit and a signal representative of a time rate of change of intracardiac impedance is applied to the peak detector circuit to determine a peak value of the rate of change.

Figure 4A:
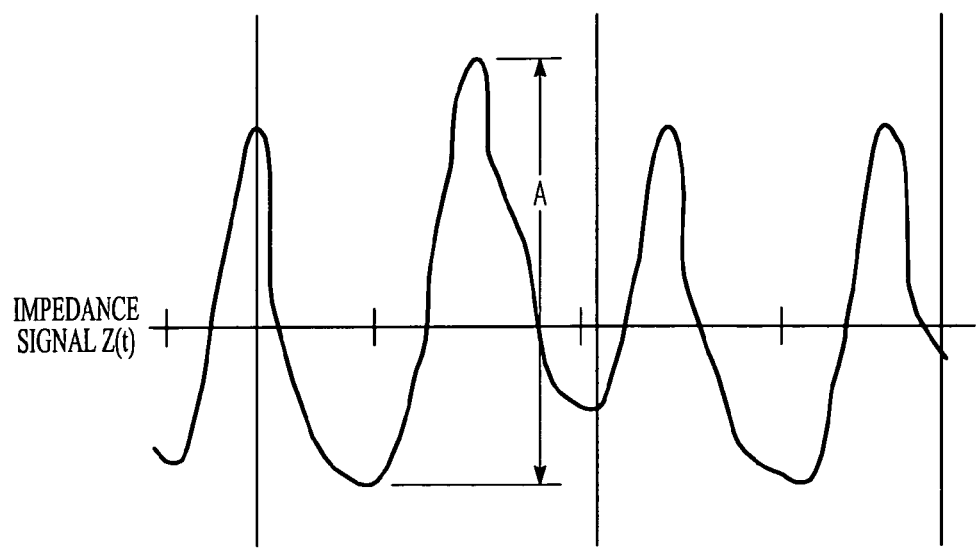
FIGS. 4A and 4B show waveforms that represents a typical impedance signal that varies in time Z(t) and its first derivative, respectively.
Figure 4B:
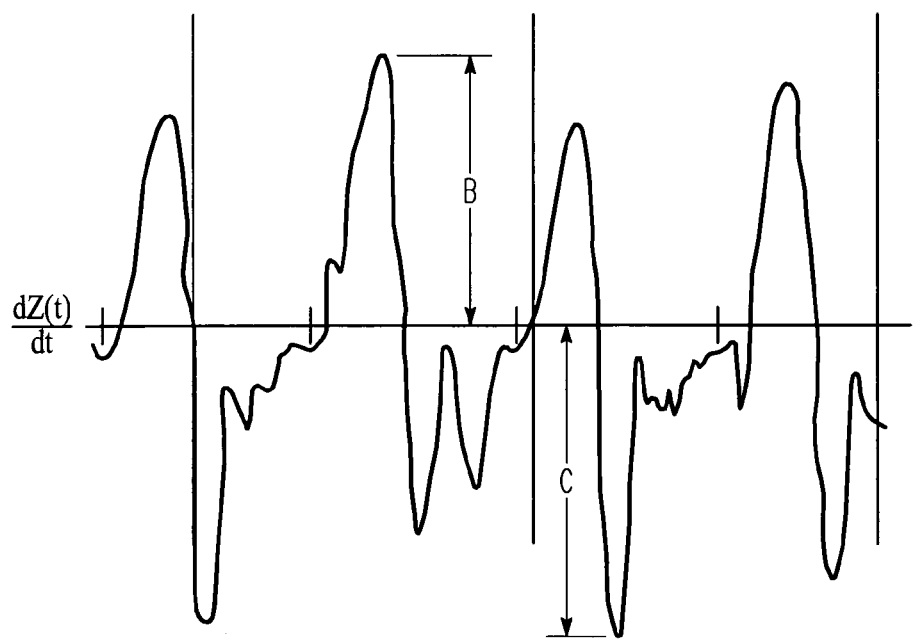

FIG. 4A shows a waveform that represents a typical signal Z(t) obtained from the impedance measurement circuit 310. The peak to peak amplitude of the waveform is labeled "A." FIG. 4B shows a waveform that represents the first derivative of the signal $$\frac{dZ(t)}{dt}.$$

The peak positive amplitude of the derivative, or the peak value of the rate of change, is labeled "B." The peak negative amplitude of the derivative is labeed "C."

Parameters that can be adjusted to increase or maximize the rate of change include parameters related to pacing therapy, parameters related to neurostimulation therapy, or parameters related to drug therapy. A non-exhaustive list of examples of pacing therapy parameters that can be adjusted include a pacing rate, pacing site or sites, the delay between pacing an atrium and a ventricle (AV delay), and the delay between pacing the two ventricles (V-V delay). For a neurostimulation device, examples of parameters to be adjusted include pulse energy, pulse duty cycle, or a stimulation site. For a drug therapy device, the adjusted parameter could be a change in a rate of infusion of an inotropic drug, such as dobutamine for example.

In some examples, the controller circuit 320 of FIG. 3 adjusts one or more parameters to increase a positive rate of change. This corresponds to improving or optimizing systolic function. In some examples, the controller circuit 320 adjusts one or more parameters to increase a magnitude of a negative rate of change. This corresponds to increasing or optimizing diastolic function. In some examples of increasing the rate of change, the controller circuit 320 adjusts at least one therapy parameter to maximize a measured peak absolute value of the intracardiac impedance time rate of change. This measured peak absolute value can be a measured peak magnitude of either an increasing or decreasing intracardiac impedance. In some examples, the peak measurement impedance includes a baseline-to-peak measurement. In some examples, the peak measurement impedance includes a peak-to-peak measurement.

According to some examples, the system 300 includes a plurality of implantable electrodes adaptable to sense electrical signals of a heart of a subject. In some examples, referring to FIG. 2, electrodes are placed in a coronary vein 220 and a right ventricle 205A. The impedance measurement circuit 310 measures intracardiac impedance between the coronary vein 220 and the right ventricle 205A using the electrodes to obtain an intracardiac impedance signal for the left ventricle 205B. In some examples, electrodes are placed in a right atrium 200A and a right ventricle 205A. The impedance measurement circuit 310 obtains an intracardiac impedance signal for the right ventricle 205A from between the electrodes placed in the right atrium 200A and the right ventricle 205A. In some examples, the electrodes are placed in a right ventricle 205A and on a left side lateral wall or free wall of the heart, such as by placement in the left anterior descending artery or by placement through the coronary sinus into a coronary vein. The impedance circuit 310 obtains an intracardiac impedance signal from between electrodes at the right ventricle 205A and the left ventricle lateral wall. Descriptions of systems and methods for multi-site impedance sensing are found in Salo et al., U.S. Pat. No. 6,278,894, entitled "Multi-Site Impedance Sensor Using Coronary Sinus/Vein Electrodes," which is incorporated herein by reference. As another example, a lead containing at least two electrodes is placed in a coronary vein 220. The impedance circuit 310 obtains an intracardiac impedance signal from between the two electrodes placed in the coronary vein. The impedance measurement will be affected by the change in ventricular wall thickness due to cardiac cycles of systole and diastole. Thus, the intracardiac impedance measurement can be used to derive the time to peak wall thickness change for the left ventricle free wall as measured from the beginning of a cardiac cycle, such as from a sensed occurrence of depolarization of atrial cells (a P-wave) for example.

According to some examples, cardiac electrodes placed in or around the heart (e.g., the right ventricle) and an electrode on the IMD (e.g., the IMED "can" electrode) are used to measure impedance. The impedance measurement circuit 310 measures the intrathoracic impedance of the heart and lungs between the cardiac electrodes and the IMD electrode. Impedance measurement circuit 310 includes a filter circuit to remove any pulmonary component of the measurement while retaining the cardiac component of the measurement.

As discussed herein, the system 300 of FIG. 3 is able to measure and monitor either systolic function, or diastolic function, or both systolic and diastolic function through measuring and monitoring the rate of change of intracardiac impedance. Because technology allows a plurality of electrodes to be placed at various locations of a heart, the controller circuit 320 is able to detect time differences between intracardiac impedance events at the different locations of the heart. Sensing impedance signals among different sets of electrodes can provide directional information regarding the propagation of intracardiac impedance signals and is sometimes referred to as sensing among different impedance vectors. In some examples, one impedance vector provides a first intracardiac impedance signals associated with a right ventricle (such as from tip electrode 235 to ring electrode 225 in FIG. 2) and a second impedance vector provides a second intracardiac impedance signals associated with a left ventricle (such as from electrode 240 placed in a right ventricle to an electrode placed in the coronary vein 220 in FIG. 2). Placement of electrodes to monitor other impedance vectors is within contemplation of the present invention.

In some examples, the controller circuit 320 determines peak values of the time rates of change of intracardiac impedance signals obtained from more than one impedance vector. The controller circuit 320 is also able to determine the difference in time between their respective peak values of the rate of change. Based on the time difference, the controller circuit 320 adjusts at least one therapy parameter in a closed loop feedback arrangement to change the difference in time, i.e., the controller circuit 320 adjusts one or more parameters to increase or (more typically) decrease the interchamber time difference. This is useful to monitor or maintain left heart and right heart synchrony.

Figure 5:
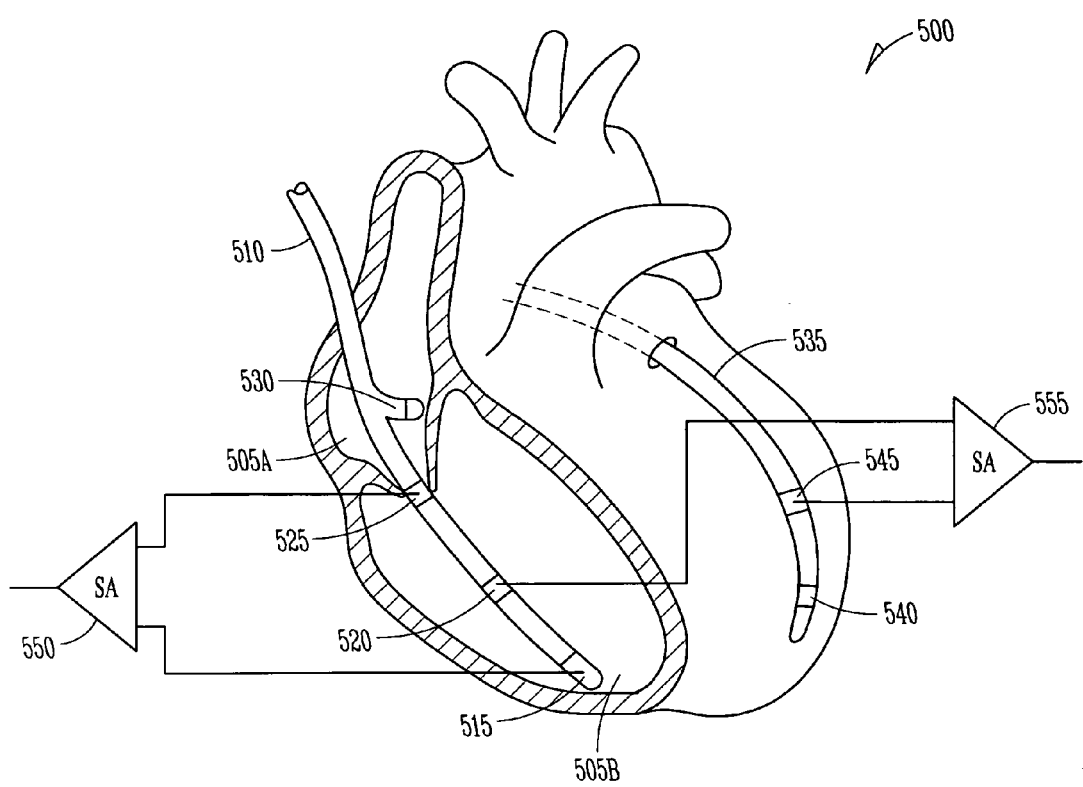
FIG. 5 is an illustration of portions of an example of a lead configuration used to monitor intracardiac impedance in both ventricles.

An example of a lead configuration 500 used with the system 300 to monitor intracardiac impedance in both ventricles is shown on FIG. 5. A first cardiac lead 510 is placed in the right atrium 505A and right ventricle 505B. The first cardiac lead includes tip electrode 515, ring electrodes 520 and 525, and atrium electrode 530. A second cardiac lead 535 is placed through the coronary sinus and into a coronary vein. The second cardiac lead 535 includes proximal ring electrode 540 and distal ring electrode 545. In some examples, the second cardiac lead is disposed via the thorax to the epicardium.

In some examples, the system 300 is able to monitor synchrony between the ventricles. A first impedance vector is between a ring electrode 520 placed in the right ventricle 505B and a ring electrode 545 placed in the coronary vein and is sensed with sense amplifier 555. The second impedance vector is between the tip electrode 515 placed in the apex of the right ventricle 505B and between the electrode 525 placed in the base of the right ventricle 505B and is sensed with sense amplifier 550. Alternatively, the first impedance vector is between the electrodes 525 and 545 and the second impedance vector is between right ventricle electrodes 515 and 525. The excitation current can be applied using the same electrodes or different electrodes such as ring electrode 520 and tip electrode 530. The controller circuit 320 of FIG. 3 uses the time to peak rate of change of the impedance vectors to determine synchrony between the left ventricle and the right ventricle. The time is measured from occurrence of a cardiac event such as, for example, from a sensed P-wave. In one example, the controller circuit 320 improves or optimizes the ventricle synchrony, as part of resynchronization therapy, by adjusting pacing times of each ventricle (i.e., interventricular pacing delay offset) to decrease or minimize the difference in time between the signals reaching their peak rate of change value. In another example, the controller circuit 320 optimizes synchrony by maximizing both positive and negative peak values of rate of change.

In some examples, the controller circuit 320 obtains the time rates of change of intracardiac impedance signals from more than one impedance vector but weighs the result measured from one impedance vector higher than the result measured by another impedance vector. For example, the controller circuit 320 may adjust parameters to improve or optimize a rate of change of intracardiac impedance measured for a left ventricle and give less weight to improving or optimizing a rate of change measured in other areas of the heart.

In some examples, the system 300 is included in a defibrillator, and the controller circuit 320 monitors intracardiac impedance as an aid in detecting tachyarrhythmia or as an aid in determining the efficacy of delivered tachyarrhythmia therapy. The controller circuit 320 uses a sudden change in a peak rate of change value along with one or more other indicia, such as a sudden increase in heart rate, to confirm an episode of ventricular tachyarrhythmia. In an example, the controller circuit 320 defines a sudden change in the value of the peak rate of change of the intracardiac impedance as a specific percentage change over a predetermined number of cardiac cycles. In some examples, the percentage and the number of predetermined cardiac cycles are programmable. If tachyarrhythmia is indicated, the controller circuit initiates or adjusts at least one therapy parameter such as initiating anti-tachycardia pacing (ATP) or activating cardioversion or defibrillation therapy.

In some examples, the system 300 is included in a neural stimulation device such as a vagal stimulation device. As an example application, a vagal stimulation device is used to control heart activity by decreasing heart contractility during a period of recovery of a patient that has suffered myocardial infarction. One possible result of myocardial infarction is a physiological compensation that increases diastolic filling pressure, i.e. backward failure. An increase in preload causes an increase in stroke volume during systole, a phenomena known as the Frank-Starling principle. Thus, heart failure can be at least partially compensated by this mechanism but at the expense of possible pulmonary and/or systemic congestion. The contractility of the heart is decreased to reduce the effect of ventricle remodeling from the increased pressure that can ultimately lead to more heart congestion. Descriptions of systems and methods to reduce or prevent the effects of ventricle remodeling through reduction of ventricular wall stress are found in Pastore et al., U.S. patent application Ser. No. 10/700,368, entitled "Multi-Site Ventricular Pacing Therapy with Parasympathetic Stimulation," filed Nov. 3, 2003, and which is incorporated herein by reference. In an example of a vagal stimulation device, the controller circuit 320 adjusts parameters related to parasympathetic nerve stimulation to optimize the peak value of the rate of change of intracardiac impedance. In some examples, the system 300 monitors the impact of reduced contractility. In some examples, the controller circuit 320 adjusts parameters to maintain the peak value of the rate of change of intracardiac impedance within a predetermined range of values.

Figure 6:
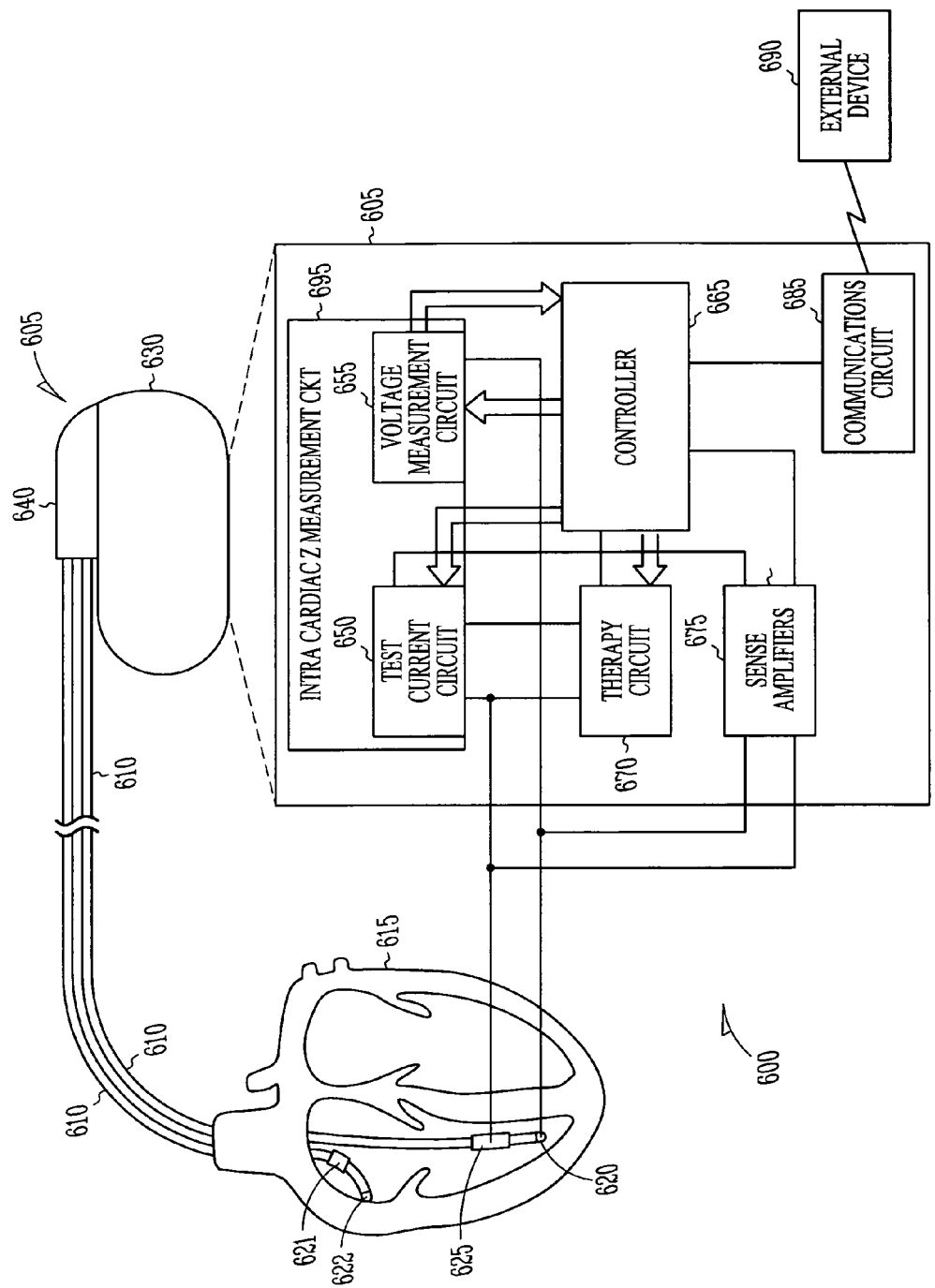
FIG. 6 is an illustration of portions of another example of a system to control cardiac therapy using sensed intracardiac impedance.

FIG. 6 is an illustration of portions of another example of a system 600 to control cardiac therapy using sensed intracardiac impedance. In this example, the system 600 includes an IMD 605 that is a cardiac rhythm management device. The IMD 605 is coupled to heart 615 by cardiac leads 610 that include lead tip and ring electrodes 620, 622, 625, 627. The cardiac leads 610 are connected to the IMD at header 640. The IMD 605 includes components that are enclosed in a hermetically-sealed canister or "can" 630. A therapy circuit 670 is used to provide cardiac function management therapy such as pacing and/or defibrillation energy in conjunction with the electrodes disposed in or around heart 615. The leads 610 and lead electrodes 620, 622, 625, 627 are used in conjunction with sense amplifiers 675 for sensing electrical activity of a heart 615.

The IMD 605 includes an intracardiac impedance measurement circuit 695 coupled to a controller 665. The impedance measurement circuit 695 includes an excitation current circuit 650 and a voltage measurement circuit 655. As an example, the excitation current is delivered between the right atrium and the right ventricle using ring electrodes 625 and 627. To determine the intracardiac impedance, the resulting voltage is measured using tip electrodes 620 and 622. Any combination of electrodes can be used to deliver the current and measure the voltage. For example, the electrodes used in FIG. 6 to deliver the excitation current and those to measure the excitation voltage could be swapped. Or, some or all of the electrodes used to deliver the current could be the same as the electrodes to measure the voltage. For example, the excitation current could be delivered from the ring electrode 625 to ring electrode 627 and the voltage could be measured from the tip electrode 620 to ring electrode 627.

In some examples, the EMD 605 further includes a memory circuit coupled to the controller circuit 665 for storing trends in measured peak values of rates of change of an intracardiac impedance signal. According to some examples, the system 600 further includes an external device 690 operable to communicate with the IMD 605 using the communication circuit 685. The communication is through wireless signals such as telemetry signals or RF signals. In some examples, the external device 690 is part of, or in communication with, a computer network such as a hospital computer network or the internet. The IMI 605 communicates wirelessly with the external device 690 and the IMD 605 communicates the trend data to the external device 690. In some examples, the external device 690 includes a display to display the trend data.

Figure 7:
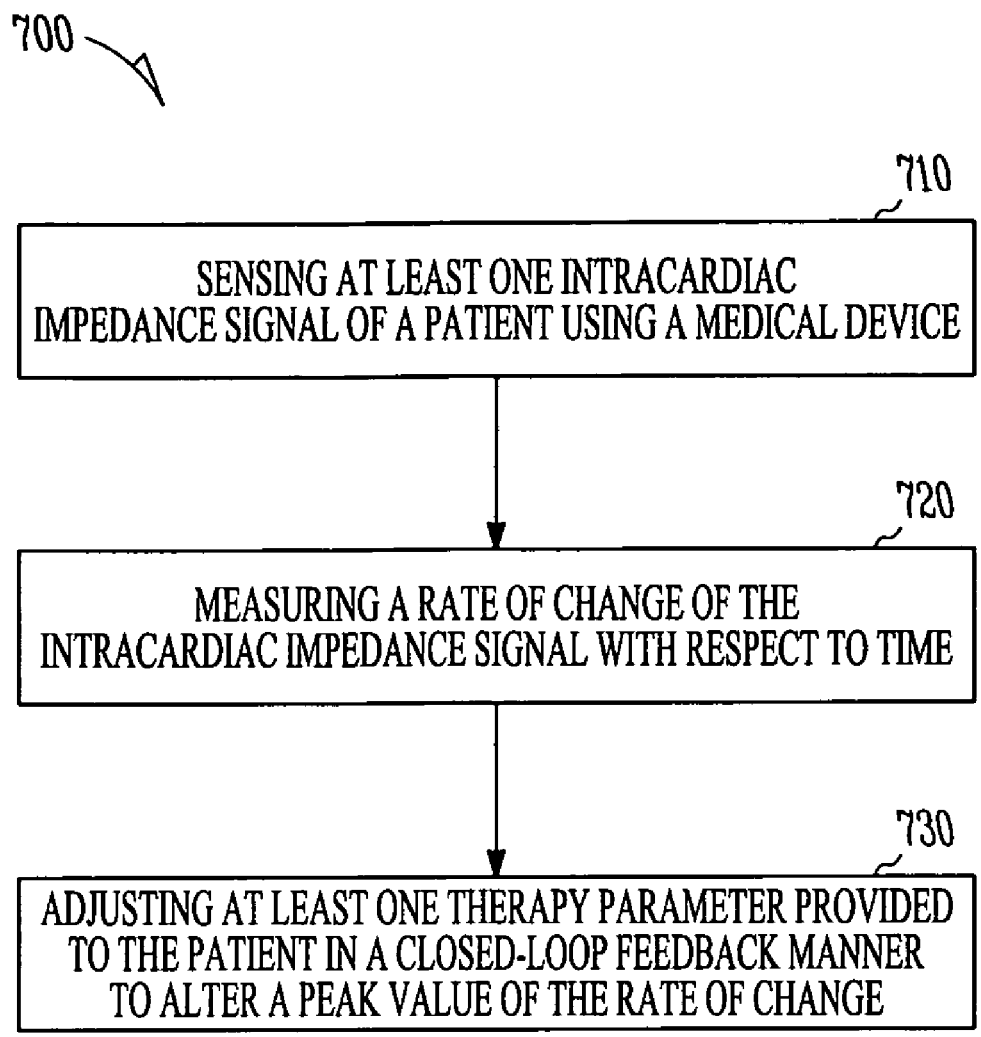
FIG. 7 is a block diagram of an embodiment of a method for controlling cardiac therapy using sensed intracardiac impedance.

FIG. 7 is a flowchart of an embodiment of a method 700 for controlling cardiac therapy using sensed intracardiac impedance. At 710, at least one intracardiac impedance signal of a patient is sensed using a medical device. In some examples the medical device is an implantable medical device (IMD). In some examples, the impedance is measured by applying an excitation current between implantable electrodes and measuring the resulting voltage between the electrodes. At 720, a rate of change of the intracardiac impedance signal with respect to time is measured. In some examples, the signal is associated with a right ventricle, or a left ventricle, or a signal sensed between the right and left ventricle. At 730, at least one therapy parameter provided to the patient is adjusted in a closed-loop feedback manner that alters a peak value of the rate of change. In some examples, the parameters are adjusted in a manner that tends to increase or maximize the rate of change. In some examples, the parameters are adjusted in a manner to decrease the peak value of the rate of change of intracardiac impedance or to maintain a peak value of the rate of change between a predetermined range of values. In some examples, adjusting at least one therapy parameter includes adjusting one or more parameters to maximize a peak absolute value of the rate of change. In some examples, adjusting includes adjusting one or more parameters to maximize a peak magnitude of a negative rate of change. In some examples, adjusting includes adjusting one or more parameters to increase a peak magnitude of both a positive rate of change value and a peak magnitude of a negative rate of change.

In some examples, sensing at least one intracardiac impedance signal includes sensing first and second intracardiac impedance signals along different first and second impedance vectors, and measuring a rate of change of an intracardiac impedance signal includes measuring rates of change of the first and second intracardiac impedance signals. As discussed previously, impedance vectors are defined by placement of implantable electrodes and the sensing of voltage signals between electrodes. In some examples, these impedance vectors include a right ventricle, a left ventricle, or both a right and left ventricle.

In some examples, adjusting at least one therapy parameter includes adjusting the difference in time between the first intracardiac impedance signal reaching its peak rate of change value and the second intracardiac impedance signal reaching its peak rate of change value. In some examples, adjusting at least one therapy parameter includes adjusting a resynchronization pacing therapy parameter to resynchronize right side and left side heart function. In some examples, adjusting at least one therapy parameter includes adjusting a resynchronization parameter to resynchronize the ventricular septum and left ventricular free wall. In some examples, adjusting at least one therapy parameter includes adjusting or changing at least one site to deliver pacing therapy, such as by switching an electrode or combination of electrodes that provides the therapy.

In some examples, the impedance signals are sensed using a medical device that provides therapy for the treatment of tachyarrhythmia. In some examples, such a medical device is implantable. Measuring the rate of change of the intracardiac impedance signal with respect to time includes monitoring peak values of measured rates of change and detecting a sudden change in a peak rate of change value together with a sudden increase in heart rate. Preferably, this is used in conjunction with other detection methods to confirm tachyarrhythmia. If tachyarrhythmia is indicated, at least one therapy parameter related to treatment of tachyarrhythmia is adjusted. In some examples, a sudden change in a peak rate of change value is defined as a percentage change in the peak rate of change value over a predetermined number of cardiac cycles. Cardiac cycles are sensed using sense amplifiers coupled to implantable electrodes.

In some examples, the method 700 further includes communicating trend data related to a time rate of change of intracardiac impedance from the medical device. In some examples, the medical device is an implantable medical device (IMD) and the data is communicated to a programmer for the IMD. In some examples, the IMD communicates data to a device in communication with a network, such as the Internet, a hospital computer network, or wireless communication network. In some examples, the IMD communicates data wirelessly to a repeater that retransmits the data over a network.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising a medical device including:
   an impedance measurement circuit adapted to be communicatively coupled to implantable electrodes to provide an intracardiac impedance signal between electrodes;
   a therapy circuit configured to deliver pacing therapy to a right ventricle and a left ventricle of a subject; and
   a controller circuit communicatively coupled to the impedance measurement circuit and the therapy circuit, wherein the controller circuit is configured to determine a time rate of change of the intracardiac impedance signal, and to adjust a time delay between pacing of the right ventricle and pacing of the left ventricle in order to controllably increase or maximize a magnitude of the time rate of change in a closed feedback loop manner.

2. The system of claim 1, wherein the controller circuit is configured to adjust the time delay between pacing of the right and left ventricles in order to controllably increase or maximize a magnitude of the negative time rate of change in a closed feedback loop manner.

3. The system of claim 1, wherein the controller circuit is configured to adjust the time delay between pacing of the right and left ventricles in order to controllably increase or maximize both a magnitude of the negative time rate of change and a magnitude of the positive time rate of change in a closed feedback loop manner.

4. The system of claim 1, wherein the impedance measurement circuit is adapted to be communicatively coupled to:
   a first set of electrodes adapted for placement to correspond to a first impedance vector at a first site of a heart of a subject; and
   a second set of electrodes adapted for placement to correspond to a different second impedance vector at a second site of the heart,
   wherein the impedance circuit is configured to provide a first intracardiac impedance signal from the first set of electrodes and a second intracardiac impedance signal from the second set of electrodes, and
   wherein the controller circuit is configured to:
       determine a time rate of change of the first and second intracardiac impedance signals; and
       adjust a time delay between pacing of the right and left ventricles in a closed loop feedback arrangement to controllably increase or maximize a magnitude of the time rate of change of both the first and second intracardiac impedance signals.

5. The system of claim 4, wherein the controller circuit is configured to controllably increase or maximize both a positive and a negative magnitude value of the time rate of change of the first and second intracardiac impedance signals.

6. The system of claim 4, wherein the first set of electrodes is adapted for placement in or near a left ventricle of the heart and the second set of electrodes is adapted for placement in a right ventricle of the heart.

7. The system of claim 4, wherein the first set of electrodes adapted for placement in a right atrium of the heart and the second set of electrodes is adapted for placement in a right ventricle of the heart.

8. The system of claim 4, wherein the controller circuit is configured to give more weight to increasing or maximizing the magnitude of the time rate of change of the first intracardiac impedance signal than to increasing or maximizing the time rate of change of the second intracardiac impedance signal.

9. A system comprising a medical device including:
   an impedance measurement circuit adapted to be coupled to implantable electrodes to obtain an intracardiac impedance signal between electrodes;
   a therapy circuit configured to deliver pacing therapy to a subject; and
   a controller circuit communicatively coupled to the impedance measurement circuit and the therapy circuit, wherein the controller circuit is configured to:
       determine a time rate of change of the intracardiac impedance signal;
       derive a time duration from a cardiac event to a time of peak wall thickness for a ventricle free wall using the time rate of change of the intracardiac impedance signal; and
       adjust a therapy parameter provided to the patient to controllably adjust the time duration in a closed feedback loop manner.

10. The system of claim 9, wherein the cardiac event includes an atrial depolarization.

11. The system of claim 9, wherein the implantable electrodes are adapted for placement in a coronary vein, and wherein controller circuit is configured to determine an occurrence of peak wall thickness of the left ventricle.

12. The system of claim 9, wherein the implantable electrodes are adapted for placement in a left anterior descending artery, and wherein controller circuit is configured to determine an occurrence of peak wall thickness of the left ventricle.

13. The system of claim 9, wherein the therapy circuit is configured to deliver pacing therapy to a right ventricle and a left ventricle of a subject; and wherein the controller circuit is configured to adjust a time delay between pacing of the right and left ventricles in order to controllably adjust the time duration.

14. The system of claim 9, wherein the therapy circuit is configured to deliver pacing therapy to an atrium and a left ventricle of a subject; and wherein the controller circuit is configured to adjust a time delay between pacing of the atrium and the left ventricle in order to controllably adjust the time duration from the cardiac event to the time of peak wall thickness.

15. A system comprising a medical device including:

an impedance measurement circuit adapted to be communicatively coupled to a first set of electrodes adapted for placement to correspond to a first impedance vector at a first site of a heart of a subject, and a second set of electrodes adapted for placement to correspond to a different second impedance vector at a second site of the heart, wherein the impedance circuit is configured to provide a first intracardiac impedance signal from the first set of electrodes and a second intracardiac impedance signal from the second set of electrodes;

a therapy circuit configured to deliver pacing therapy to a right ventricle and a left ventricle of a subject; and a controller circuit communicatively coupled to the impedance measurement circuit and the therapy circuit, wherein the controller circuit is configured to:

derive a time to a peak value of the rate of change of the first intracardiac impedance signal and a time to a peak value of the rate of change of the second intracardiac impedance signal, and adjust a time delay between pacing of the right and left ventricles in a closed loop feedback arrangement to controllably decrease or minimize a difference in the time to peak values.

16. The system of claim 15, wherein the controller circuit is configured to measure the time to peak values relative to a sensed atrial depolarization.

17. The system of claim 15, wherein the controller circuit is configured to determine a peak value using the peak-to-peak value of a time rate change of an intracardiac impedance value.

18. The system of claim 15, wherein the controller circuit is configured to determine a peak value using the baseline-to-peak value of a time rate change of an intracardiac impedance value.

19. The system of claim 15, wherein the first set of implantable electrodes includes an electrode adapted for placement in a right ventricle, and the second set of implantable electrodes include an electrode adapted for placement in a coronary vein.

20. The system of claim 15, wherein the first set of implantable electrodes include an electrode adapted for placement in a right ventricle and the second set of implantable electrodes include an electrode adapted for placement in a left anterior descending artery.

* * * * *